United States Patent [19]
Garcia

[11] Patent Number: 5,833,675
[45] Date of Patent: Nov. 10, 1998

[54] IRRIGATOR DEVICE

[76] Inventor: Teddy Garcia, 921 Blanding Blvd., Orange Park, Fla. 32065

[21] Appl. No.: 821,401

[22] Filed: Mar. 20, 1997

[51] Int. Cl.$^6$ ..................................................... A61M 7/00
[52] U.S. Cl. ............................ 604/310; 604/290; 239/229
[58] Field of Search .............................. 604/19, 151, 290, 604/310; 239/229, 243, 333

[56] References Cited

U.S. PATENT DOCUMENTS 4,892,526  1/1990  Reese ........................................ 604/290

Primary Examiner—Michael Buiz
Assistant Examiner—Julian W. Woo
Attorney, Agent, or Firm—Thomas C. Saitta

[57] ABSTRACT

An irrigator device, and in particular an ear canal irrigation device, comprising a hand-held pump bottle, a conduit tube connected to the pump bottle, an end tube connected to the conduit tube, where the end tube has an internal bore of much smaller diameter than the internal bore of the conduit tube, and where the end tube is composed of a highly flexible material such that it will oscillate when water is pumped through it.

16 Claims, 2 Drawing Sheets

IRRIGATOR DEVICE

BACKGROUND OF THE INVENTION

This invention relates generally to the field of devices for irrigating or cleaning a body cavity or wound, and in particular for irrigating and cleaning the ear canal, by supplying a pressurized stream of water and directing the water stream into the interior of the cavity, wound or ear canal, such that debris is loosened and flushed out of the cavity wound or canal. More particularly, the invention relates to such devices which utilize a hand-held and hand-operated sprayer, a main conduit tube ending in a reduced-diameter, flexible, end tube and a transparent splash shield affixed to the conduit tube.

In circumstances where the production of ear wax exceeds the body's natural ability to maintain an open ear canal, it is necessary to physically remove the excess ear wax which has built up in the ear canal. Several types of devices are known to accomplish this task. One type of device is a metal scraping tool, such as a wire loop on a handle. The physician inserts the end of the tool into the ear canal and uses the wire loop to loosen and remove the ear wax. The use of a metal tool is not the best solution, due to the sensitivity of the ear canal and ear drum. An alternative method is to use a syringe filled with water, where the physician inserts the tip end of the syringe into the ear canal and expels a stream of water against the ear wax. Control of the syringe is awkward, and the water stream cannot be accurately aimed nor can it be easily oscillated within the canal. In a similar manner, mechanical pumps can be used to provide the pressurized water stream, but these devices suffer the same drawbacks as the syringe with regard to control and effectiveness. These types of devices are also used to irrigate and clean body cavities or wounds.

It is an object of this invention to provide an irrigation device, and primarily an ear canal irrigation device, which has improved operational characteristics relative to the known irrigation devices. It is a further object to provide such a device which is easy to handle, provides controlled means for delivering bursts of pressurized water, includes an oscillation means insertable in the ear canal, wound or body cavity such that the water stream strikes at varying angles with changing locations, has a conduit tube of small enough outer diameter to prevent blockage of the flushing water exiting the ear canal, cavity or wound, and provides a transparent splash guard to prevent splatter of water and debris while allowing the physician to observe the proper placement of the device.

SUMMARY OF THE INVENTION

The device is an irrigator which delivers a pressurized stream of water into an ear canal, body cavity or wound in small volume bursts of short duration, and is primarily an ear irrigator used for irrigating and cleaning the ear of excess wax and other debris. The device comprises in general a hand-held pump bottle containing a volume of water, the pump bottle operated by a trigger pump actuated by squeezing the trigger, a main conduit tube connected to the outlet of the pump bottle, a transparent splash shield affixed to and encircling the main conduit tube, and an end tube, preferably flexible and oscillating, connected to the free end of the main conduit tube, the end tube being of reduced outer and inner diameter relative to the main conduit tube. The transition from a relatively large internal bore in the main conduit tube to a small internal bore in the end tube creates a high velocity flow at the tip and causes the end tube to oscillate during the delivery of the water stream. The oscillating motion creates a pulsing water stream relative to any particular location in the ear canal and is much more effective in removing ear wax and debris than a steady stream of water. Because the end tube is of small diameter, the device does not impede water flow out of the ear canal.

BRIEF DESCRIPTION OF THE DRAWINGS

FIG. I is a side view of the invention.

DETAILED DESCRIPTION OF THE INVENTION

With reference to the drawings, the invention will now be described in detail with regard for the best mode and preferred embodiment. In general, the device is an irrigator comprising a hand-held pump or spray bottle which contains a volume of water or other liquid, a squeeze trigger for producing a stream of water, a main conduit connected to the pump bottle having a transparent splash shield mounted thereon, and a preferably highly flexible, short, thin end tube connected to the free end of the main conduit tube. The device is primarily adapted for use as an ear canal irrigator, and the description following will focus on that application, although it is to be understood that the device may also be used for irrigation and cleaning of body cavities or wounds.

Figure 1:
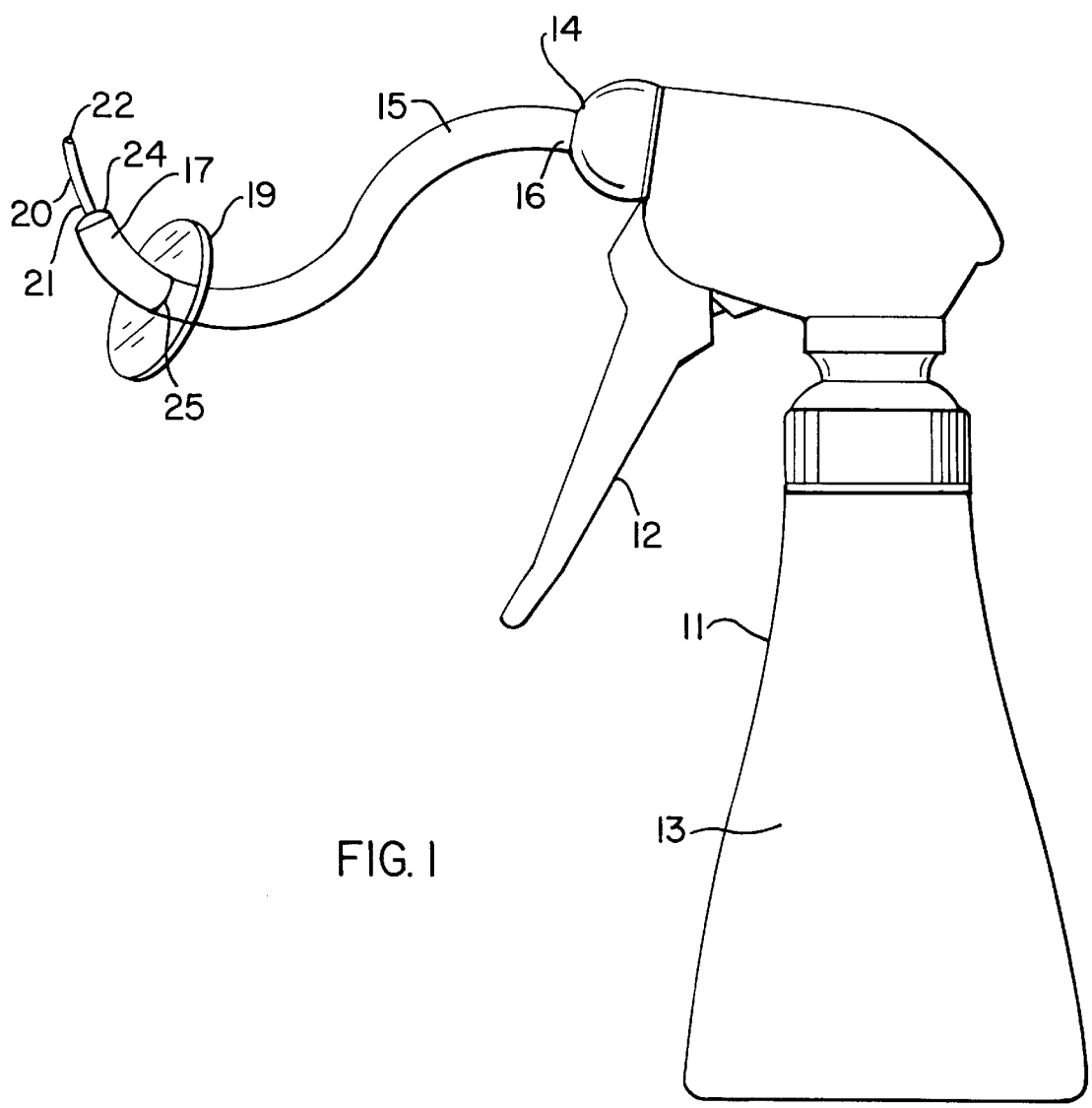

Referring now to FIG. 1, the device is seen to comprise a pump or spray bottle 11 of a suitable size to be held in one hand, the pump bottle 11 comprising a reservoir 13 to retain a quantity of water or other liquid to be directed into the ear canal. Operation of a squeeze pump trigger 12 of known construction forces a stream of water from the reservoir 13 out through the bottle outlet 14. The attached end 16 of the main conduit tube 15 is connected to the bottle outlet 14, such that the expelled water passes through the conduit tube internal bore 18 to the conduit free end 17. Preferably, conduit tube 15 is composed of a flexible, plastic material, but conduit tube 15 may also be made of a rigid plastic or metal.

Figure 2:
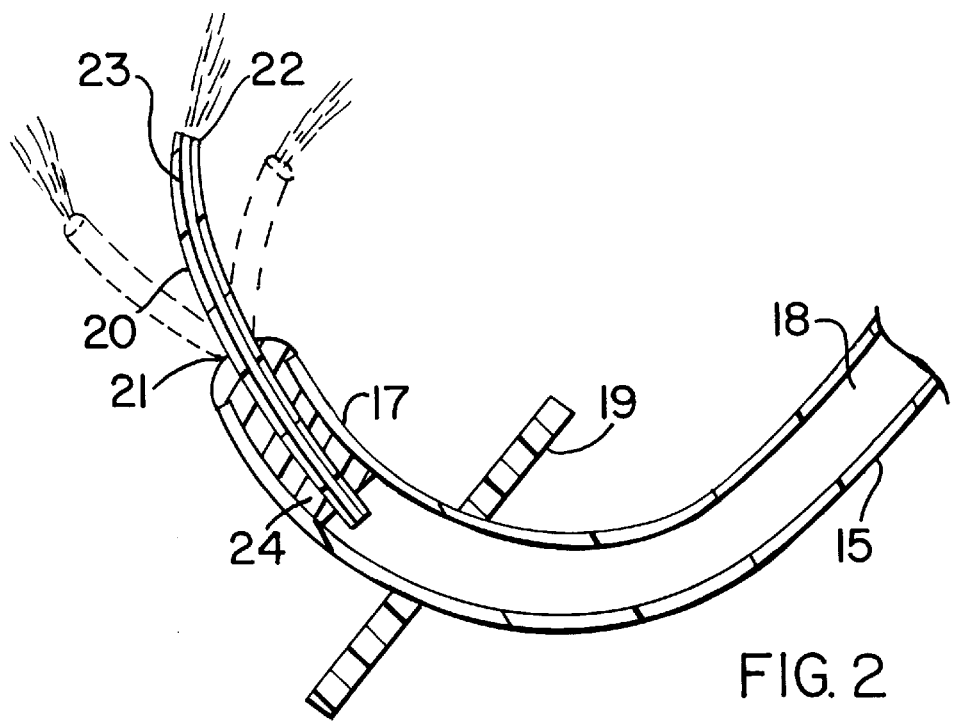
FIG. 2 is a cross-sectional view of the conduit portion of the invention.

A relatively short segment of flexible, plastic tube material forms end tube 20, which has a tip end 22 and a connected end 21. Alternatively, the end tube 20 may be semi-rigid or rigid, but this construction would greatly reduce the desirable oscillating effects produced by the device. Connected end 21 is inserted into the internal bore 18 at the free end 17 of conduit tube 15. The internal bore 23 of end tube 20 and preferably the outer diameter of end tube 20 as well are both smaller than the internal bore 18 of conduit tube 15. The end tube 20 is joined to the conduit tube 15 by a reducing connector 24, as shown in FIG. 2. For example, with a conduit tube 15 having an internal bore 18 of ¼ inch diameter, the outer diameter of end tube 20 is approximately ⅛ inch in diameter and the internal bore 23 of end tube 20 is preferably of about 1/16 inch diameter. The conduit tube 15 is of much greater length than the end tube 20. For example, conduit tube 15 may be approximately 4 inches long with an end tube 20 of only ½ inch. The plastic material composing the end tube 20 must be very flexible so that the tip 22 will oscillate freely when water is pumped through the internal bore 23.

A splash guard 19, preferably transparent to allow the physician to observe the positioning of the device during use, is mounted externally to the conduit tube. The splash guard 19 is preferably circular and provided with an axial aperture 25 which allows it to be slid onto the conduit tube 15, the axial aperture 25 being slightly smaller than the outer diameter of the conduit tube 15 so that it will remain in one position unless shifted by the physician. The splash guard 19 is positioned near the free end 17 of the conduit tube 15 to block spray or splash erupting from the ear canal.

Figure 3:
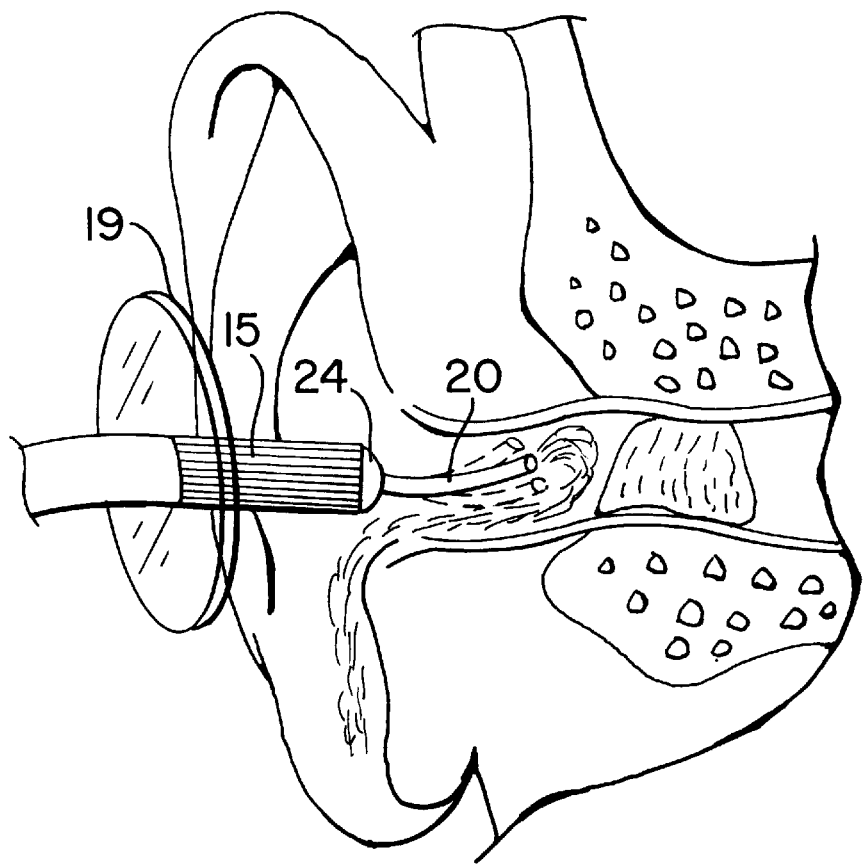
FIG. 3 is a view of the conduit portion of the invention as inserted into the ear canal.

The device is used as shown in FIG. 3. The end tube 20 is inserted into the ear canal and the free end 17 of the main conduit tube 15 is positioned just external to the ear canal, the physician using one hand to hold the pump bottle 11 and the other to position the conduit tube 15. When the squeeze trigger 12 is depressed, water is forced into the internal bore 18 of the conduit tube 15, where it encounters the reducing connector 24 and the reduced size internal bore 23 of the end tube 20. This reduction in internal diameter creates a pressure build-up, whereby the water exiting the tip 22 of the end tube 20 is at relatively high velocity. This high velocity causes the thin, flexible end tube 20 to oscillate within the ear canal, as illustrated by the dashed line positions in the figure. This oscillating action sweeps and pulses the water stream, thereby loosening ear wax and debris in a highly efficient manner. The small outer diameter of the end tube 20 allows the water and flushed debris to flow from the ear canal without impediment.

It is understood that equivalents and substitutions to the components described above may be obvious to those skilled in the art, and the true scope and definition of the invention therefore is to be as set forth in the following claims.

I claim:

1. An irrigation device comprising a hand-held pump bottle having a reservoir to contain a liquid, an outlet and a squeeze trigger to force said liquid from said reservoir through said outlet; a conduit tube having a free end, an internal bore and an attached end connected to said outlet; an end tube having a tip end, an internal bore and a connected end joined to said free end of said conduit tube, where said end tube internal bore has a smaller diameter than said conduit tube internal bore, and further where said end tube is composed of a flexible plastic material such that when said water is forced from said reservoir it passes through said conduit tube internal bore and into said end tube internal bore and causes said tip end of said end tube to oscillate.

2. The device of claim 1, where said conduit tube is composed of a flexible material.

3. The device of claim 1, where said end tube is much shorter than said conduit tube.

4. The device of claim 1, where said conduit tube internal bore has a diameter of approximately ¼ inch and said end tube internal conduit has a diameter of approximately ¹⁄₁₆ inch.

5. The device of claim 1, where said end tube is joined to said conduit tube by a reducing connector.

6. The device of claim 1, further comprising a splash guard mounted on said conduit tube.

7. The device of claim 6, where said splash guard is transparent.

8. The device of claim 1, where said conduit tube is approximately 4 inches in length and said end tube is approximately ½ inch in length.

9. An irrigation device comprising a hand-held pump bottle having a reservoir to contain a liquid, an outlet and a squeeze trigger to force said liquid from said reservoir through said outlet; a conduit tube having a free end, an internal bore and an attached end connected to said outlet; an end tube having a tip end, an internal bore and a connected end joined to said free end of said conduit tube, where said end tube internal bore has a smaller diameter than said conduit tube internal bore and where said end tube is of smaller outer diameter than said conduit tube.

10. The device of claim 9, where said conduit tube is composed of a flexible material.

11. The device of claim 9, where said end tube is much shorter than said conduit tube.

12. The device of claim 9, where said conduit tube internal bore has a diameter of approximately ¼ inch and said end tube internal conduit has a diameter of approximately ¹⁄₁₆ inch.

13. The device of claim 9, where said end tube is joined to said conduit tube by a reducing connector.

14. The device of claim 9, further comprising a splash guard mounted on said conduit tube.

15. The device of claim 14, where said splash guard is transparent.

16. The device of claim 9, where said conduit tube is approximately 4 inches in length and said end tube is approximately ½ inch in length.

* * * * *